United States Patent [19]
Hansen et al.

[11] Patent Number: 5,756,000
[45] Date of Patent: May 26, 1998

[54] PERFLUORO(ALKOXYCYCLOALKANE) CARBONYL FLUORIDE COMPOSITIONS AND THEIR USE

[75] Inventors: John C. Hansen, Lakeland; George G. I. Moore, Afton; Stephen D. Polson, St. Paul; Patricia M. Savu, Maplewood; Richard M. Stern, Woodbury, all of Minn.

[73] Assignee: Minnesota Mining and Manufacturing Company, St. Paul, Minn.

[21] Appl. No.: 595,924

[22] Filed: Feb. 6, 1996

[51] Int. Cl.$^6$ .............. B01F 17/00; C07C 235/40
[52] U.S. Cl. .............. 252/307; 252/3; 252/351; 252/355; 252/356; 252/357; 564/142; 564/191; 564/281; 564/297; 560/125; 562/30; 562/83
[58] Field of Search ............ 564/194, 142, 564/143, 297, 209, 281, 201, 191; 562/507, 109, 113, 30, 104, 106, 83; 560/125; 252/356, 3, 351, 307, 353, 354, 355, 357

[56] References Cited

U.S. PATENT DOCUMENTS

| | | | |
|---|---|---|---|
| 2,519,983 | 8/1950 | Simons | 205/430 |
| 2,567,011 | 9/1951 | Diesslin et al. | 560/227 |
| 2,593,737 | 4/1952 | Diesslin et al. | 562/507 |
| 2,713,593 | 6/1955 | Brice | 562/586 |
| 3,600,433 | 8/1971 | Holland et al. | 560/125 |
| 3,644,513 | 2/1972 | Sweeney et al. | 564/209 |
| 3,686,288 | 8/1972 | Holland et al. | 564/191 |
| 4,992,471 | 2/1991 | Longhurst | 514/613 |
| 5,085,786 | 2/1992 | Alm et al. | 252/8.05 |
| 5,322,904 | 6/1994 | Bierschenk et al. | 525/331.6 |
| 5,354,901 | 10/1994 | Flynn et al. | 562/507 |
| 5,362,919 | 11/1994 | Costello et al. | 568/601 |
| 5,466,877 | 11/1995 | Moore | 562/852 |

FOREIGN PATENT DOCUMENTS

| | | | |
|---|---|---|---|
| 0 201 193 | 12/1986 | European Pat. Off. | C07C 103/737 |
| 0 190 847 | 8/1996 | European Pat. Off. | C07C 61/15 |

OTHER PUBLICATIONS

Kirk–Othmer, *Encyclopedia of Chemical Technology*, "Surfactants and Detersive Systems," 3rd ed., vol. 22, pp. 332–347, John Wiley & Sons, New York (1979).

Nagase, *Fluorine Chemistry Reviews*, "Electrochemical Fluorination," vol. 1, pp. 77–106, Marcel Dekker, Inc., New York (1967).

*Fluorine Chemistry*, edited by Dr. J.H. Simons, vol. 1, pp. 416–419, Academic Press Inc., New York, (1950).

Abe et al., *Preparation, Properties, and Industrial Applications of Organofluorine Compounds*, "Electrochemical Fluorination (Simons Process)", pp. 19–43, John Wiley & Sons, New York (1982).

Kirk–Othmer, *Encyclopedia of Chemical Technology*, "Fluorinated Higher Carboxylic Acids" 4th ed., vol. 11, pp. 551–559, John Wiley & Sons, New York (1994).

*Primary Examiner*—Richard D. Lovering
*Assistant Examiner*—Daniel S. Metzmaier
*Attorney, Agent, or Firm*—John A. Burtis

[57] ABSTRACT

This invention provides perfluoro(alkoxycycloalkane) carbonyl fluoride compounds wherein, pendant from the fluorinated ring, are from 2 to 5 perfluoroalkoxy groups having from 1 to 4, preferably 1 to 2, carbon atoms with the proviso that when one or more of the perfluoroalkoxy groups contain from 3 to 4 carbon atoms, there are no more than 3 pendant groups.

In yet another aspect, this invention provides aqueous film-forming foam (AFFF) compositions comprising one or more perfluoro(alkoxycycloalkane) carbonyl group-containing surfactants and one or more water-soluble fluorine-free surfactants selected from the group consisting of nonionic hydrocarbon-containing surfactants with a hydrophilic-lipophilic balance (HLB) value greater than or equal to about 10 and ionic hydrocarbon-containing surfactants having a carbon chain length containing inclusively from about 6 to about 10 carbon atoms.

20 Claims, No Drawings

5,756,000

PERFLUORO(ALKOXYCYCLOALKANE) CARBONYL FLUORIDE COMPOSITIONS AND THEIR USE

FIELD OF THE INVENTION

This invention relates to perfluoro(alkoxycycloalkane) carbonyl fluoride compositions, their preparation and their use. In another aspect, the present invention relates to the use of perfluoro(alkoxycycloalkane)carbonyl fluoride compositions to prepare perfluoro(alkoxycycloalkane) carbonyl group-containing compounds. In yet another aspect, this invention relates to aqueous film-forming foamable solutions.

BACKGROUND OF THE INVENTION

Surfactants, as that term is generally known and used, are surface-active compounds characterized by certain defining features in structure and property. See, for example, 22 Kirk-Othmer Encyclopedia of Chemical Technology 332–36 (3d ed. 1979). Among such defining features, surfactants as a class are amphipathic in structure, composed of groups having opposing solubility tendencies. The most common surfactants are composed of two such groups, an oleophilic hydrocarbon chain and a water solubilizing ionic group. Surfactants are widely used throughout industry and enjoy a wide variety of application. Surfactants may be used for any application requiring those properties characteristic of surface-active agents: detergency, foaming, wetting, emulsifying, solubilizing, and dispersing.

A commercially-important class of surfactants comprises that containing one or more fluorochemical moieties and one or more water solubilizing polar moieties. Typically, such surfactants are formed by reacting one or more fluorochemical compounds with one or more water solubilizing compounds, where the fluorochemical compounds are formed as the product of a fluorination reaction of a hydrocarbon, typically alkyl, precursor. The fluorination reaction used to produce the fluorochemical intermediate compounds typically is carried out by electrochemical fluorination with hydrogen fluoride, and is less frequently carried out using direct fluorination with elemental fluorine. Electrochemical fluorination of ether-containing compounds, the preferred method of fluorination, is, however, generally characterized by low yield. See, e.g., T. Abe & S. Nagase, *Electrochemical Fluorination (Simons Process) as a Route to Perfluorinated Organic Compounds of Industrial Interest*, 19, 28–29 in PREPARATION, PROPERTIES AND INDUSTRIAL APPLICATIONS OF ORGANOFLUORINE COMPOUNDS (R. E. Banks ed., 1982), reporting yields of perfluorodialkyl ethers from their corresponding dialkyl ethers of much less than 50 percent, and Patricia M. Savu, *Fluorinated Higher Carboxylic Acids*, 11 KIRK-OTHMER ENCYCLOPEDIA OF CHEMICAL TECHNOLOGY 551 (4th ed. 1994), noting generally poor yields obtained from the electrochemical fluorination of ethers.

SUMMARY OF THE INVENTION

Briefly, in one aspect, this invention provides perfluoro(alkoxycycloalkane) carbonyl fluoride compounds wherein, pendant from the fluorinated ring, are from 2 to 5 perfluoroalkoxy groups having from 1 to 4, preferably 1 to 2, carbon atoms with the proviso that when one or more of the perfluoroalkoxy groups contain from 3 to 4 carbon atoms, there are no more than 3 pendant groups.

In another aspect, the present invention provides perfluoro(alkoxycycloalkane) carbonyl group-containing surfactants according to the formula:

$$(A_fY)_x(Q)(Z)_x \quad (I)$$

wherein:

$A_f$ is a perfluoro(alkoxycycloalkane) carbonyl radical where, pendant from the fluorinated ring, are from 1 to 5, preferably 2 to 5, perfluoroalkoxy groups having from 1 to 4, preferably 1 to 2, carbon atoms with the proviso that when one or more of the perfluoroalkoxy groups contain from 3 to 4 carbon atoms, there are no more than 3 pendant groups;

Y is an oxygen or a sulfur atom or is an N(R') group where R' is selected as a hydrogen atom, a lower alkyl group, or comprises a water-solubilizing polar group that contains an anionic, cationic, nonionic, or amphoteric moiety (or any combination thereof) connected to the nitrogen atom by a multivalent linking group;

Q is a multivalent, generally divalent, linking group;

Z is a water-solubilizing polar group containing an anionic, cationic, nonionic, or amphoteric moiety or any combination thereof; and x is independently 1 or 2.

In another aspect, this invention provides aqueous film-forming foam (AFFF) compositions comprising one or more perfluoro(alkoxycycloalkane) carbonyl group-containing surfactants and one or more water-soluble fluorine-free surfactants selected from the group consisting of nonionic hydrocarbon-containing surfactants having a hydrophilic-lipophilic balance (HLB) value greater than or equal to about 10 and ionic hydrocarbon-containing surfactants having a carbon chain length containing inclusively from about 6 to about 16 carbon atoms.

DETAILED DESCRIPTION OF THE INVENTION

The preferred perfluoro(alkoxycycloalkane)carbonyl fluoride compositions described by the present invention include those according to the formula:

wherein:

$R_f$ is independently selected as a perfluoroalkyl group having from 1 to 4 carbon atoms; and n is an integer from 2 to 5 inclusive with the proviso that when $R_f$ contains from 3 to 4 carbon atoms, n is less than or equal to 3.

Carbonyl compositions, such as those depicted by Formula II, may be prepared by fluorinating an alkoxybenzoyl derivative, e.g. an alkoxybenzoic acid, alkoxybenzoic ester, alkoxybenzoic amide, or preferably an alkoxybenzoyl halide. The fluorination may be carried out either by electrochemical fluorination (ECF) with hydrogen fluoride as described by U.S. Pat. No. 2,519,983 (Simons), or by direct fluorination with elemental fluorine as described by U.S. Pat. No. 5,362,919 (Costello et al.), both of whose descriptions are hereby incorporated by reference. Preferably, the reaction is carried out by electrochemical fluorination to produce the carbonyl fluoride compositions of the invention in as high as 50 to 70% yield.

The fluorination reaction of the alkoxybenzoyl precursor may be depicted by the following reaction where the reaction is carried out through electrochemical fluorination:

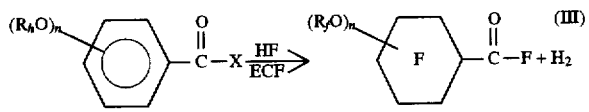

wherein:

$R_h$ is independently selected as an alkyl group having from 1 to 4 carbon atoms;

$R_f$ is independently selected as a perfluoroalkyl group having from 1 to 4 carbon atoms, such as defined for Formula II;

X is a hydroxy, an alkoxy, a halogen atom (preferably a chlorine or fluorine atom), or is an $N(R'')_2$ group where $R''$ is independently selected as a hydrogen atom or a lower alkyl group; and n is an integer between 2 and 5 inclusive as defined for Formula II.

It will be understood that in carrying out electrochemical fluorination of 6-membered ring precursor compounds, a minor amount of ring opening and ring contraction typically occur. For the purposes of the present invention, this phenomena will result in perfluoroalkoxy-substituted 5-membered ring by-products, which are difficult to separate by distillation because they have very nearly identical boiling points as the principal 6-membered ring products. The presence of these 5-membered ring by-products is not detrimental to compositions of the present invention; they react to produce useful derivative products analogous to those produced by the reactions of the principal 6-membered ring products. Details of ring contraction in the context of electrochemical fluorination may be found in PREPARATION, PROPERTIES AND INDUSTRIAL APPLICATIONS OF ORGANOFLUORINE COMPOUNDS (R. E. Banks ed., 1982).

The electrochemical fluorination reaction can be carried out by electrochemically fluorinating, by the "Simons Process," a conductive solution of the organic starting material in anhydrous liquid hydrogen fluoride in an electrolytic cell. The fluorination product can be removed from the cell as part of the gaseous effluent. The effluent can be cooled to condense and collect or recover the aforementioned saturated and partially- or fully-fluorinated ethers. Any unreacted HF or by-products can also be condensed and recycled to the cell.

The "Simons process" or the "Simons electrochemical fluorination process" is a known, commercially-practical process for reacting anhydrous HF with certain classes of organic compounds. An early patent describing such technology is U.S. Pat. No. 2,519,983 (Simons), which contains a drawing of a Simons cell and its appurtenances, and a description and photograph of laboratory and pilot plant cells appear at pages 416–418 of Vol. 1 of "*Fluorine Chemistry*", edited by J. H. Simons, published in 1950 by Academic Press, Inc., New York. Electrochemical fluorination by the Simons process is also described by S. Nagase in Fluorine Chem. Rev., 1 (1) 77–106 (1967), and by T. Abe et al. in Chapter 1 of "Preparation, Properties, and Industrial Applications of Organofluorine Compounds," R. E. Banks, editor, Ellis Horwood Ltd., Holsted Press (1982).

Generally, in a relatively large-scale setting, a Simons cell useful in the practice of this invention comprises a cell body, typically made of carbon steel and usually provided with a cooling jacket, in which is suspended an electrode pack comprising series of alternating and closely-spaced cathode plates (typically made of iron, nickel, or nickel alloy) and anode plates (typically made of nickel), the plates being immersed in the current-conductive solution of the organic starting material in essentially anhydrous hydrogen fluoride. Gaseous cell effluent comprising the volatilized electrochemically fluorinated ether product and volatized hydrogen fluoride can be withdrawn from the cell as an overhead via a valved-outlet line. The cell is operated with the conductive solution containing a desired relative concentration of the organic starting material (the alkoxybenzoyl precursor), typically between 5 and 30 percent, that will result in the production of the desired saturated, fully-fluorinated or partially-fluorinated product. The relative temperatures and pressures under which the cell is operated will be those conditions conducive to the production of the desired fluorinated product. Generally, by increasing the concentration of organic starting material in the conductive solution (and thereby decreasing the concentration of the HF reactant), the hydrogen-content of the resulting fluorinated products is increased, the reaction mixture in a sense being "starved" for HF. Generally, the temperature of the cell during the electrochemical fluorination can be in the range of 0° to 70° C., preferably 20° to 60° C. In operation, the cell can be run at a pressure in the range of 760 to 4000 torr, preferably in the range from 1000 to 3000 torr. The cell can be operated at average applied direct current at cell voltages in the range of 4 to 9 volts and current densities in the range of 10 to 100, preferably 20 to 80, mAmp/cm$^2$ of active anode surface (where the electrolysis takes place). The cell can be operated either at constant current or constant voltage. The concentration of the organic starting material in the anhydrous hydrogen fluoride generally will be 5 to 30 weight percent. The reactor gaseous effluent, comprising the fluorinated adduct, hydrogen fluoride, hydrogen, and other gaseous products, can be withdrawn from the top of the reactor and passed to a condenser system, as described supra. Other details of the Simons electrochemical fluorination process and cell will be omitted here in the interest of brevity, and the disclosure of such technology in the above-cited references to such technology can be referred to for descriptions of such detail, whose descriptions are herein incorporated for such purpose.

The above-described alkoxybenzoyl precursors may also be fluorinated by direct fluorination using known methods. U.S. Pat. No. 5,362,919 (Costello et al.) whose description is hereby incorporated by reference describes one such useful method. According to this method, a diluted solution of the organic precursor material in a normally liquid, inert medium is directly contacted with a stoichiometric excess of fluorine gas, $F_2$, which preferably is diluted with an inert gas such as nitrogen, in a temperature-controlled reactor to perfluorinate the alkoxybenzoyl precursor at a temperature and a flow rate of inert gas (if used) sufficient to volatilize by-product hydrogen fluoride, HF. The hydrogen fluoride is removed from the reactor as it is produced (and is not recycled) so that the fluorination is substantially carried out in a hydrogen fluoride-free environment. The resultant solution or dispersion of perfluorinated organic substance is then separately removed from the reactor. The perfluorinated product, using this method, can be separated from the inert medium, e.g. by distillation, to obtain the perfluorinated product as the product of the process. Other details of this preferred method of direct fluorination and details of other useful methods of direct fluorination are omitted in the interest of brevity, as those details are well-known and established in the art.

In accordance with a second aspect of this invention, a class of cationic, amphoteric, anionic, and nonionic surfactants may be derived from the above-described perfluoro (alkoxycycloalkane)carbonyl fluoride compounds by reacting carbonyl fluorides such as those depicted by Formula II with various water-solubilizing nucleophiles. Of the class of surfactants made in accordance with this invention, cationic and amphoteric fluoroaliphatic surfactants are preferred; amphoteric amine oxide surfactants are particularly preferred.

The preferred cationic and amphoteric fluoroaliphatic surfactants are readily prepared by first reacting an N,N-disubstituted alkylene diamine, e.g., 3-(N,N-dimethylamino)propylamine (DMAPA), 2-(N,N-dimethylamino)ethylamine, 3-(N,N-diethylamino)propyl amine, or 6-(N-ethyl,N-methylamino)hexylamine, with a carbonyl fluoride of the class described supra to form a perfluoro(alkoxycycloalkane) carboxamidoamine intermediate compound of the formula:

$$A_f NHC_m H_{2m} N(R)_2 \quad (IV)$$

wherein:

$A_f$ is a perfluoro(alkoxycycloalkane) carbonyl radical where, pendant from the fluorinated ring, are from 1 to 5, preferably 2 to 5, perfluoroalkoxy groups having from 1 to 4, preferably 1 to 2, carbon atoms with the proviso that when one or more of the perfluoroalkoxy groups contain from 3 to 4 carbon atoms, there are no more than 3 pendant groups;

R is a lower alkyl group having from 1 to 4 carbon atoms; and m is inclusively an integer between 2 and 6.

As described in U.S. Pat. No. 3,686,288 to Holland et al., whose description is incorporated herein by reference, such a reaction may be carried out by slowly adding the carbonyl fluoride to the diamine composition in an inert solvent such as diethyl ether, tetrahydrofuran, dioxane, toluene, N,N-dimethyl formamide, diisopropyl ether, or an alkane, e.g. hexane.

The intermediate amidoamine may subsequently: (1) be either protonated with an inorganic halogen acid (e.g., HCl or HBr), a sulfur-containing inorganic acid (e.g., sulfuric acid),an organic carboxylic acid (e.g., $CH_3COOH$), or an organic sulfonic acid (e.g., benzene sulfonic acid) or be quaternized with an alkylating agent (e.g., an alkyl halide or $C_2H_5OSO_2OC_2H_5$) to form a cationic fluoroaliphatic surfactant; (2) be reacted with a sultone (e.g., gamma-propane sultone), a lactone (e.g., gamma-butyrolactone), a carboxy-functional acrylate (e.g. acrylic acid), a sulfonato-functional acrylate (e.g., N-(3-sulfo-2,2-dimethylpropyl)acrylamide) or a similar compound to form an amphoteric zwitterionic fluoroaliphatic surfactant; or (3) be reacted with an oxidizing agent (e.g., hydrogen peroxide) to form the most preferred amphoteric amine oxide surfactant; the details of such reactions being well-known and established in the art.

The cationic, anionic, nonionic, and amphoteric fluoroaliphatic surfactants of the invention may be depicted generally by the following formula:

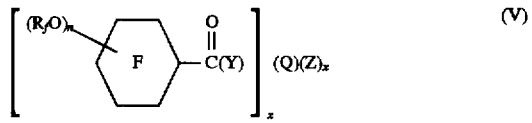

wherein:

$R_f$ is independently selected as a perfluoroalkyl group having from 1 to 4 carbon atoms;

n is an integer from 1 to 5 inclusive with the proviso that when $R_f$ contains from 3 to 4 carbon atoms, n is less than or equal to 3;

Y is an oxygen or a sulfur atom or is an N(R') group where R is selected as a hydrogen atom, a lower alkyl group, or comprises a water-solubilizing polar group that contains an anionic, cationic, nonionic, or amphoteric moiety (or any combination thereof) connected to the nitrogen atom by a multivalent linking group;

Q is a multivalent, generally divalent, linking group such as a substituted or unsubstituted alkylene (e.g., ethylene, n-propylene, or iso-butylene), an arylene (e.g., phenylene), a combination of an alkylene and an arylene (e.g., xylylene), an oxydialkylene (e.g., $CH_2CH_2OCH_2CH_2$), a thiodialkylene (e.g., $CH_2CH_2SCH_2CH_2$), or-may be non-existent (i.e., replaced by a single bond). The Q group of any particular surfactant will depend on the specific reactants used in its preparation;

Z is a water-solubilizing polar group containing an anionic, cationic, nonionic, or amphoteric moiety or any combination thereof. Typical anionic Z groups include $CO_2H$, $CO_2M$, $SO_3H$, $SO_3M$, $OSO_3H$, $OSO_3M$, $(OCH_2CH_2)_n OSO_3M$ (n=1–5), $OPO(OH)_2$, and $OPO(OM)_2$, wherein M is a metallic ion such as sodium, potassium, or calcium, or is an ammonium or another such nitrogen-based cation. Typical cationic Z groups include $NR'''_3A'$, where R''' is independently selected as a lower alkyl group, a hydroxyalkyl group, or a hydrogen atom and where A' is an anion such as chloride, iodide, sulfate, phosphate, acetate, citrate or hydroxide. Representative nonionic Z groups include polyoxyethylene alcohols and glycols (e.g., $O(CH_2CH_2O)_7CH_3$ and $O(CH_2CH_2O)_{14}H$), and mixed polyoxyethylene/polyoxypropylene alcohols and polyols.

Typical amphoteric Z groups include $N^+(CH_3)_2O^-$, $N^+(CH_3)_2CH_2CH_2COO^-$ and $N^+(CH_3)_2CH_2CH_2CH_2SO_3^-$; and x is independently 1 or 2.

The surfactants of the present invention, when dissolved in aqueous solutions, achieve remarkably low surface tensions at low critical micelle concentration (CMC) values. Preferred surfactants are those in which more than one perfluoroalkoxy group is attached to the perfluorinated cyclohexane ring (i.e. n>1 as depicted in Formula V) to impart maximum surface activity. The most preferred surfactants contain three trifluoromethoxy groups attached to the 3, 4, and 5 positions on the perfluorocyclohexane ring, imparting the highest attained surface activity.

The surfactants made in accordance with this invention may be used for any application requiring a surface active agent, including uses as protective coatings and similar applications. Those surfactants detailed herein find particular utility in the formulation of aqueous film-forming foam (AFFF) concentrates such as those used to extinguish hydrocarbon and other flammable liquid fires. Concentrated aqueous fluorochemical surfactant-containing solutions that produce an aqueous film-forming foam upon dilution to a premix (typically with 94 to 99 percent fresh or sea water) and aeration, must possess a combination of critical properties to be effective in extinguishing flammable liquid fires. Upon dilution, the premix must exhibit superior foaming characteristics to produce a thick foam blanket that achieves rapid knock down, control, extinguishment, and resistance to reignition of the fire and persists for a significant time after the fire's extinguishment. Aqueous solutions comprising the fluorochemical surfactants detailed supra are useful as concentrates for producing a film-forming foam. Because of the remarkably low surface tensions achieved by these fluorochemical surfactants, the surface tension of these aqueous solutions is depressed well below the surface tension of a flammable liquid so that a vapor-sealing film draining from their foam readily spreads over the flammable liquid. As a consequence, films produced by these solutions have a strong tendency to reform if disturbed or broken thereby reducing the tendency of a fire to reignite where the film has been disturbed, for example, by wind blowing over the surface of the foam.

The aqueous film-forming foamable solutions of the invention comprise an aqueous solution of one or more fluorochemical surfactants depicted by Formula I and one or more water-soluble substantially fluorine-free surfactants. Useful fluorine-free surfactants include, used either individually or as blends with one another, nonionic hydrocarbon-containing surfactants that have a hydrophilic-lipophilic balance (HLB) value of greater than or equal to about 10 and short-chain ionic hydrocarbon-containing surfactants having a carbon chain length containing inclusively from about 6 to about 10 carbon atoms. Representative nonionic fluorine-free surfactants include ethylene oxide-based nonionic surfactants such as $C_nH_{2n+1}O(C_2H_4O)_mH$ where n is an integer between about 8 and 18 and m is greater than or equal to about 10; ethoxylated alkylphenols such as

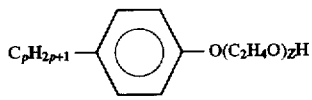

where p is an integer between about 4 and about 12 and z is greater than or equal to about 10, and block copolymers of ethylene oxide and propylene oxide such as Pluronic™ F-77 surfactant (containing at least about 30 wt % ethylene oxide) available from BASF Corp., Wyandotte, Mich. Representative ionic fluorine-free surfactants include alkyl sulfates, e.g., sodium octyl sulfate and sodium decyl sulfate; alkyl ether sulfates and alkyl sulfonates, e.g., $C_nH_{2n+1}(OC_2H_4)_2OSO_3Na$ ($6 \leq n \leq 10$) and $C_nH_{2n+1}SO_3Na$ ($6 \leq n \leq 10$); salts of an n-octyl amine di-propionic acid, e.g., $C_8H_{17}N(CH_2CH_2COOM)_2$ where M is sodium or potassium; and those imidazole-based surfactants described in U.S. Pat. No. 3,957,657 (Chiesa, Jr.), whose description is hereby incorporated by reference.

While any of the fluorochemical surfactants described herein may be employed in the AFFF concentrates of the invention, amphoteric fluorochemical surfactants are preferred, the amphoteric amine oxide surfactants being particularly preferred. One or more additional fluoro-aliphatic amphoteric and/or anionic surfactants, such as a fluorinated aminocarboxylate or a perfluoroalkane sulfonate, may also be added to the formulation. Such additional surfactants are described in U.S. Pat. No. 5,085,786 (Alm et al.), whose description is also incorporated herein by reference.

Additional components may optionally be added to the AFFF formulations such as water soluble solvents to facilitate solubilization of the fluorochemical surfactant or surfactants including ethylene glycol, glycerol, butyl Carbitol™, dipropylene glycol mono-n-propyl ether, dipropylene glycol monomethyl ether, and hexylene glycol. These solvents may also act as foam stabilizers and freeze-protection agents. Additional components, such as stabilizers and thickeners, can be incorporated into the concentrates of the invention to enhance the foam stability property of the foam produced from aeration of the aqueous solution of the concentrate. Examples of stabilizers and thickeners are partially hydrolyzed protein, starches, polyvinyl resins, e.g., polyvinyl alcohol, polyvinyl pyrolidone, polyacrylamides, carboxyvinyl polymers, alkanol amides, long chain alkanols, and poly(oxyethylene)-glycol. In particular, polysaccharide resins, such as xanthan gum, can be incorporated as foam stabilizers in concentrates where such concentrates will be used on polar solvent fires such as alcohols, ketones, and ethers. Additional components that may be added to the AFFF formulations of the invention are detailed in U.S. Pat. Nos. 5,085,786 (Alm et al.) and 3,772,195 (Francen), both of whose descriptions are incorporated herein by reference for such purpose.

In practice of the aqueous film-forming foam concentrates, water delivered through a fire hose under pressure induces typically 3 percent by volume of the fluorochemical concentrate solution into the hose line by venturi effect to form a premixture (or "premix") of the concentrate diluted with water. The premix becomes aerated to produce a foam by use of an air-aspirating nozzle located at the outlet end of the hose. The foam is applied to a body of burning fuel or other flammable liquid and spreads quickly as a blanket on the surface for rapid extinguishment. As the foam on the surface of the flammable liquid drains, an aqueous film is formed which, if disturbed or broken, tends to reform to seal hot vapors and prevents reignition of the fire. The concentrate solutions of the invention are considered highly storage stable, passing the U.S. Government specification (MIL-F-24385C) requiring that foaming and film-forming properties of concentrates not be adversely affected if the concentrate and its fresh and sea water premixes (i.e., the concentrate diluted with water) are stored at 65° C. for 10 days, designed to simulate a room temperature storage period of approximately 10 years.

Typically, between 1 and 10 percent by weight of the fluorochemical surfactant or surfactants and between 1 and 10 percent by weight of the fluorine-free surfactant or surfactants will be employed to make the foamable aqueous concentrate solution. The total amount of solids attributable to other additive components, if such components are present, should be such that the aqueous solution maintains its foamability and such that the density of the foam prepared therefrom is less than about 1 g/cc. Generally, the amount of solids attributable to said optional components will be less than about 40 weight percent, preferably less than about 30 weight percent, of the foamable aqueous solution.

The following examples are offered to aid in a better understanding of the present invention. These examples are not to be construed as an exhaustive compilation of all embodiments of the present invention and are not to be unnecessarily construed as limiting the scope of this invention.

EXAMPLES

Synthesis of Perfluoro(alkoxycycloalkane)carbonyl Fluoride Compositions

Example 1

Using an electrochemical fluorination cell of the type described in U.S. Pat. No. 2,713,593 (Brice et al.), a mixture of 93.5% (wt) anisoyl (4-methoxybenzoyl) chloride and 6.5% (wt) dimethyldisulfide (DMDS) was electrochemically fluorinated in boiling HF at 2000 torr and 50° C. contained in a 2500 mL cell equipped with a 0.20 m² nickel anode for a total time of 50.2 hours using an average current of 102 amps and average conductivity of 5.8 volts during the electrofluorination. The production rate of crude perfluorinated carbonyl fluoride was about 40% of theoretical, according to a GC/FTIR analysis of an aliquot derivatized into the methyl ester. The crude liquid perfluorinated product was mixed with 65 g of powdered NaF, the NaF was allowed to settle, and 1319 g of the treated crude perfluorinated carbonyl fluoride was decanted into a 3-L flask fitted with overhead stirrer, thermometer, and simple distillation head.

Upon distillation, 1252 g of distillate was recovered at atmospheric pressure, a head temperature of 92°–105° C. and a pot temperature of 105°–160° C. GC/FTIR analysis of an aliquot of distillate derivatized into the methyl ester showed the distillate to consist of 65% perfluorinated carbonyl fluoride, primarily:

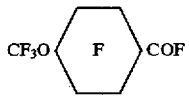

with the remainder being non-functional perfluorinated materials (inerts). After conversion to its corresponding amide by reaction with 3-(N,N-dimethylamino) propylamine, GC mass spectral analysis showed this material to consist of the following: 19.9% $CF_3OC_6F_{12}CONH(CH_2)_3N(CH_3)_2$ (open chain materials, three isomers), 73.9% of $CF_3OC_6F_{10}CONH(CH_2)_3N(CH_3)_2$ (cyclohexyl and methyl cyclopentyl materials, seven isomers), and 3% $C_6H_{11}CONH(CH_2)_3N(CH_3)_2$ (material missing ether link).

Example 2

A mixture of 90% (wt) methyl 3,4-dimethoxybenzoate and 10% (wt) DMDS was electrochemically fluorinated in boiling HF at 2000 torr and 50° C. contained in a 2500 mL cell equipped as described for Example 1 but containing a 0.063 m² nickel anode. Enough extra DMDS was continually added during the run to bring the total amount of HF added to 16% (wt) of the total amount of organic added. The cell run lasted for a total of 507.5 hours using an average current of 24 amps and average conductivity of 6.5 volts during the electrochemical fluorination. The production rate of crude perfluorinated carbonyl fluoride was about 30% of theoretical, according to GC/FTIR analysis of the methyl ester derivative. The crude liquid perfluorinated product was mixed with 250 g of powdered NaF, the NaF was allowed to settle, and 3021 g of the treated crude perfluorinated carbonyl fluoride was decanted into a 3-L flask fitted with overhead stirrer, thermometer, and simple distillation head. Upon distillation, 2115 g of distillate was recovered at atmospheric pressure, a head temperature of 102°–121° C. and a pot temperature of 105°–160° C. GC/FTIR analysis of an aliquot of distillate derivatized to the methyl ester showed the distillate to consist of 65% of the carbonyl fluoride shown below with the remainder being inerts.

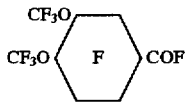

Example 3

A mixture of 90% (wt) 3,4,5-trimethoxybenzoyl chloride and 10% (wt) DMDS was electrochemically fluorinated in boiling HF at 2000 torr and 50° C. contained in a 2500 mL cell equipped as described for Example 1 but containing a 0.063 m² nickel anode. Enough extra DMDS was added during the run to bring the total amount of HF added to 11–12% (wt) of the total amount of organic added. The cell run lasted for a total of 346.3 hours using an average current of 26 amps and average conductivity of 6.5 volts during the electrochemical fluorination. The production rate of crude perfluorinated carbonyl fluoride was about 30% of theoretical, according to a GC/FTIR analysis of an aliquot derivatized into the methyl ester. The crude liquid perfluorinated product was mixed with 125 g of powdered NaF, the NaF was allowed to settle, and 2565 g of the treated crude perfluorinated carbonyl fluoride was decanted into a 3-L flask fitted with overhead stirrer, thermometer, and simple distillation head. Upon distillation, 1898 g of distillate was recovered at atmospheric pressure, a head temperature of 102°–135° C. and a pot temperature of 105°–160° C. GC/FTIR analysis of an aliquot of distillate derivatized into the methyl ester showed the distillate to consist of 65% of the carbonyl fluoride:

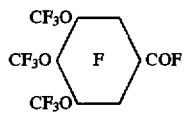

with the remainder being inerts.

Example 4

A mixture of 80% (wt) 4-butoxybenzoic acid and 20% (wt) DMDS was electrochemically fluorinated in boiling HF at 1280 to 1790 torr and 35° to 40° C. contained in a 1500 mL cell equipped as described for Example 1 but containing a 0.037 m² anode and additionally containing approximately 300 g of $C_6F_{14}$. The cell run lasted a total of 193.3 hours using an average current of 12.0 amps and average conductivity of 6.7 volts. According to GC/FTIR analysis of an aliquot derivatized into the methyl ester, small amounts (about 5% of theoretical) of the desired perfluorinated carbonyl fluoride:

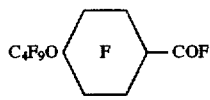

were produced.

Example 5

A mixture of 90% (wt) 2-ethoxybenzoic acid and 10% (wt) DMDS was electrochemically fluorinated in boiling HF at 1800 torr, 45° C. contained in a 750 mL cell containing a 0.037 m² anode and equipped and run as previously described for Example 4. The cell run lasted a total of 165.8 hours using an average current of 16.0 amps and average conductivity of 5.8 volts. According to GC/FTIR analysis of an aliquot derivatized into the methyl ester, a 18% yield of the desired perfluorinated carbonyl fluoride:

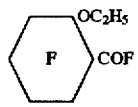

was produced.

Example 6

A mixture of 90% (wt) 4-ethoxybenzoic acid and 10% (wt) DMDS was electrochemically fluorinated in boiling HF at 1540 to 1790 torr and 45° C. contained in a 750 mL cell containing a 0.037 m² anode equipped and run as previously described for Example 4. The cell run lasted a total of 351 hours using an average current of 12.1 amps and average conductivity of 6.9 volts. According to GC/FTIR analysis of an aliquot derivatized into the methyl ester, a 26% yield of the desired perfluorinated carbonyl fluoride:

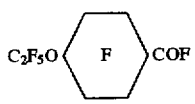

was produced.

Example 7

The direct fluorination apparatus was exactly as described in U.S. Pat. No. 5,362,919. The 2-liter reactor was filled with $CFCl_2CF_2Cl$ and a mixture of 160 mL/min $F_2$ and 1000 mL/min $N_2$ was bubbled through the stirred liquid. Methyl 3,4,5-trimethoxybenzoate (55.0 g) was dissolved in 50 mL $CHCl_3$ and diluted to 350 mL final volume with 1,1,1-trifluorotrichloroethane. This mixture was fed at 17.5 mL/hr into the reactor. The reactor temperature was controlled at 18° C. by jacket cooling. After 40 minutes, the fluorine flow was reduced to 150 mL/min. After the completion of addition at about 20 hours, the reactor was purged with $N_2$ before removal of the contents, indicated by IR absorption at 1830 $cm^{-1}$ to be a solution of perfluoro methyl (3,4,5-trimethoxy) cyclohexanecarboxylate. A larger scale repetition of this reaction on 383 g in a 5 gallon reactor gave a residue of 702 g after stripping the solvent. Treatment of this with 0.25 g pyridine as described in U.S. Pat. No. 5,466,877, caused a vigorous evolution of a gas (assumed to be $COF_2$) and conversion of about half of the liquid from the perfluoroester (IR 1831 $cm^{-1}$) to the carbonyl fluoride (IR 1876 $cm^{-1}$). Addition of 0.67 g more pyridine and occasional shaking gave complete conversion by the next day. An aliquot was reacted with methanol and analyzed by GLC, indicating three major isomers of the title material, with very minor lower molecular weight products. The fluorocarbon layer was separated from the pyridine and distilled to 440.3 g (49%) boiling at 140°–165° C. F-NMR indicated 8.7 F of $CF_3O$ groups per F of carbonyl fluoride group, indicating a high degree of conversion to the desired product.

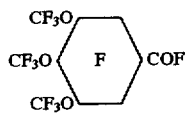

Example 8

In a similar fashion to Example 7, 900 g methyl 4-methoxybenzoate was fluorinated in two batches by dissolving 450 g in 90 g dimethoxyethane and 1500 mL $CFCl_2CF_2Cl$, then feeding these batches to a stirred 5 gallon reactor containing $CFCl_2CF_2Cl$ and purged with a gas mixture of 1 Lpm $F_2$ and 4.25 Lpm $N_2$. The temperature was maintained at 18° C. The $CFCl_2CF_2Cl$ was distilled from each batch after completion. The combined residues weighed 2545 g. Addition of 0.5 mL pyridine to 679.1 g caused evolution of gas and complete conversion (1890 $cm^{-1}$ IR). This residue (561 g) was distilled to a main cut of 269.6 g (57% yield) at 100°–125° C. GLC of the methyl ester showed two main peaks, presumed isomers of the desired material:

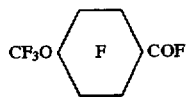

Example 9

Using an electrochemical fluorination cell of the type described in U.S. Pat. No. 2,713,593 (Brice et al.), a mixture of 80% (wt) 3,4-diethoxybenzoic acid and 20% (wt) dimethyldisulfide (DMDS) was dissolved in anhydrous HF to a final concentration of 48.7% and was electrochemically fluorinated in a 1500 mL cell equipped with a 0.063 $m^2$ nickel anode and containing about 300 g $C_6F_{14}$ at 1280 torr and 35° C. for a total time of 141.5 hours using an average current of 11.4 amps and average conductivity of 6.7 volts during the electrofluorination. The production rate of the desired perfluorinated carbonyl fluoride:

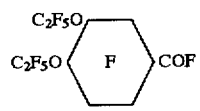

was about 4% of theoretical, according to a GC/FTIR analysis of an aliquot derivatized into the methyl ester.

Example 10

Using an electrochemical fluorination cell of the type described in U.S. Pat. No. 2,713,593 (Brice et al.), a mixture of 95% (wt) methyl 2,6-dimethoxybenzoate and 5% (wt) DMDS was dissolved in 51.3% anhydrous HF and was electrochemically fluorinated in a 1500 mL cell equipped with a 0.063 $m^2$ nickel anode using a continuous feed system at 2310 torr and 55° C. for a total time of 214.2 hours using an average current of 20 amps and average conductivity of 6.8 volts during the electrofluorination. The production rate of the desired perfluorinated carbonyl fluoride:

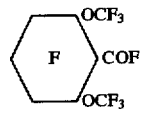

was about 37% of theoretical.

Comparative Example C1

Comparative Example C1:

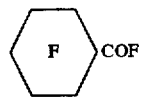

was prepared according to the following method.

The electrochemical fluorination of benzoyl chloride (2517 g) was carried out in a Simons cell of about 2300 cc using 5% DMDS. The nickel anode used was 0.167 $m^2$ in area. The average pressure was 1000 torr to 1300 torr at an average cell temperature of 35° C. for a total of 435.4 hours at an average current of 18.3 amps at 5.2 volts. The organic was fed semi-continuously for the length of the run at about 5.78 g/hour or about 101% theoretical based upon current passed. A total of 3700 g of products were collected from a −40° C. condenser at a rate of 0.404 g/amp hour of current. Analysis of the products by GC indicated about 73% of the desired acyl fluorides.

Comparative Example C2

Comparative Example C2:

was prepared according to the following method.

The electrochemical fluorination of toluyl chloride O was carried out in a Simons cell of about 2300 cc in volume, using 10% dimethyldisulfide additive. The cell was run at an average of 5.8 volts, 83 amps average current, using a nickel anode with about 0.167 m² in area, at 2000 torr control and at 48° C. for a total of 280.7 hours. The organic feed was fed semi-continuously to the cell at a rate of about 90.1% theoretical based upon current, and the products were collected from the overhead −40° C. condenser/decanter. GC/FTIR analysis indicated about 66% purity of the desired perfluoro acyl fluoride corresponding to a 58% theoretical yield based upon current passed.

Synthesis of Perfluoro(alkoxycycloalkane)carbonyl Fluoride Amidoamine Compositions Example 11

To a flask fitted with an overhead stirrer, thermometer, and simple distillation head and containing 76 g (0.75 mole) of 3-(N,N-dimethylamino)propylamine and 400 g of isopropyl ether was added, with stirring, 242 g (0.40 mole) of the compound made in Example 1. During the addition of the acid fluoride, the flask was cooled in an ice bath in order to keep the temperature of the contents of the flask to below 15° C. After the addition of the acid fluoride was completed, the reaction mixture was stirred at room temperature for four hours. When after four hours the reaction was determined to be complete based on GC analysis, 400 mL of deionized water was added with stirring, the stirring was discontinued after 15 minutes, and the contents of the flask was allowed to separate into an upper and a lower phase. The upper product-containing phase was saved and was washed two times with 400 mL of water. The isopropyl ether was then removed from the product phase using a rotary evaporator to give 207 g of crude product. The crude product was vacuum distilled at 0.01 torr and at a head temperature of 89°–110° C. to give 187 g of purified product. Gas chromatography/mass spectral analysis showed this purified product to contain approximately 74% of the desired product:

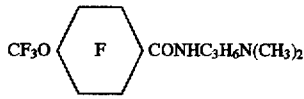

as described in Example 1.

Example 12

Example 12:

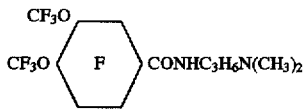

was prepared using the same procedure as described for Example 11 except that the compound made in Example 2 was substituted for that made in Example 1.

Example 13

Example 13:

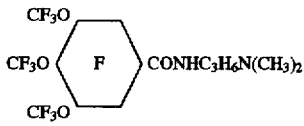

was prepared using the same procedure as described for Example 11 except that the compound made in Example 3 was substituted for that made in Example 1.

Example 14

Example 14:

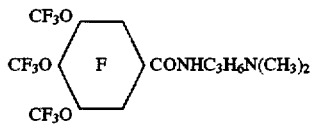

was prepared using the same procedure as described for Example 11 except that the compound made in Example 7 (the intermediate made using direct fluorination) was substituted for that made in Example 1 (the intermediate made using electrochemical fluorination).

Comparative Example C3

Comparative Example C3:

was prepared using the same procedure as described for Example 11 except that the compound made in Comparative Example C1 was substituted for that made in Example 1.

Comparative Example C4

Comparative Example C4:

was prepared using the same procedure as described for Example 11 except that the compound made in Comparative Example C2 was substituted for that made in Example 1.

Synthesis and Evaluation of Perfluoro(alkoxycycloalkane)carbonyl Group-Containing Surfactants Example 15

12.16 g (0.02 mole) of the compound made in Example 13, 5.7 g (0.05 mole) of 30% aqueous hydrogen peroxide and 12.0 g of ethanol were added to a 3-necked round-bottom flask equipped with stirrer, thermometer and water condenser. This mixture was stirred and heated at 60° C. for 2 hours and was allowed to cool overnight. The mixture was then refluxed for 4 hours, 0.2 g of decolorizing/activated charcoal was added, and the mixture was refluxed for an additional 2 hours. The solution was filtered through Celite™ filter aid and the filtrate was evaporated to dryness using a rotary evaporator to produce a waxy solid. The completion of reaction was confirmed by dissolving a small amount of the solid in deionized water and raising the pH of the aqueous solution to 8 using dilute aqueous sodium hydroxide. The solution stayed clear with no precipitate of amidoamine starting material evident, indicating a completion of reaction to form:

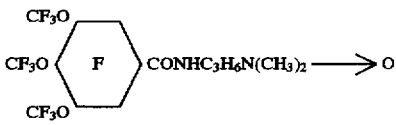

Example 16
Example 16:

was prepared using the same procedure as described for Example 15 except that 0.02 mole of the compound made in Example 14 (derived from direct fluorination cell product) was substituted for 0.02 mole of the compound made in Example 13.

Example 17
Example 17:

was prepared using the same procedure as described for Example 15 except that 0.02 mole of Example 12 was substituted for 0.02 mole of Example 13.

Example 18
Example 18:

was prepared using the same procedure as described for Example 15 except that 0.02 mole of Example 11 was substituted for 0.02 mole of Example 13.

Comparative Example C5

41.0 g (0.1 mole) of the compound made in Comparative Example C3, 40.0 g of ethanol and 22.7 g (0.22 mole) of 30% aqueous $H_2O_2$ were added to a 3-necked round-bottom flask equipped with a stirrer. This mixture was stirred for 1 hour at 70° C., was mildly refluxed for an additional 2 hours, and was allowed to sit overnight. The next day, the mixture was refluxed for another 2 hours, approximately 0.5 g of activated carbon was added, and the mixture was refluxed for another 2 hours. The mixture was filtered through Celite™ filter medium and the water and ethanol were evaporated off overnight using a nitrogen stream to give the desired surfactant:

Comparative Example C6

23.0 g (0.05 mole) of the compound made in Comparative Example C4, 25.0 g of ethanol and 12.0 g (0.106 mole) of 30% aqueous $H_2O_2$ were added to a 3-necked round-bottom flask equipped with a stirrer. While initially stirring for 5 minutes, the mixture exothermed slightly to 27° C. The mixture was heated briefly to 40° C., followed by stirring at ambient temperature for 16 hours, then refluxing for 2 hours and allowing the mixture to cool slightly. Then approximately 0.2 g of activated carbon was added, and the mixture was refluxed for an additional 2.5 hours. The mixture was filtered through Celite™ filter medium, the activated carbon was washed with a mixture of water and ethanol, and the solvents were distilled off using a rotary evaporator. The resulting wet solid was further dried in a vacuum oven to give the desired surfactant:

Example 19

12.16 g (0.02 mole) of the compound made in Example 13, 5.4 g of isopropanol and 1.6 g (0.022 mole) of acrylic acid were added to a 3-necked round-bottom flask equipped with a stirrer. This mixture was stirred for 14 days at room temperature. The solution remained clear over the time of the reaction, with no crystals or precipitate forming. Most of the isopropanol was evaporated using a rotary evaporator, and the remaining volatile constituents were stripped by placing the sample in an aspirator vacuum oven set at 70° C. for 4 hours to give a viscous, dark brown liquid. The completion of reaction was confirmed by dissolving a small amount of the dark brown liquid in deionized water and raising the pH of the aqueous solution to 8 using dilute aqueous sodium hydroxide. The solution stayed clear with no precipitate of amidoamine evident, indicating good completion of reaction to form:

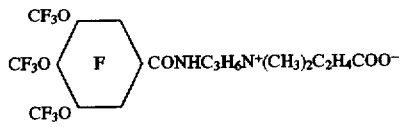

Example 20

Example 20:

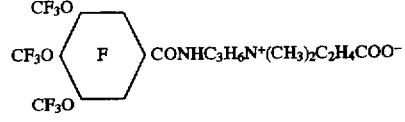

was prepared using the same procedure as described for Example 19 except that 0.02 mole of the compound made in Example 14 (derived from direct fluorination cell product) was substituted for 0.02 mole of the compound made in Example 13 (derived from electrochemical fluorination cell product).

Comparative Example C7

Comparative Example C7:

was prepared using the same procedure as described for Example 19 except that 0.02 mole of the compound made in Comparative Example C3 was substituted for 0.02 mole of the compound made in Example 13.

Comparative Example C8

Comparative Example C8:

was prepared using the same procedure as described for Example 19 except that 0.02 mole of the compound made in Comparative Example C4 was substituted for 0.02 mole of the compound made in Example 13.

Example 21

10.3 g (0.0217 mole) of the compound made in Example 11 and 2.7 g (0.0217 mole) of gamma-propane sultone were added to a 3-necked round-bottom flask equipped with a stirrer and thermometer. The mixture was heated to 80° C. with stirring, when an exotherm to 135° C. occurred. The temperature was kept at 135° C. for 15 minutes, then the contents of the flask were allowed to cool to room temperature, 13.0 g of a cream-colored solid formed upon cooling, which was broken up with a spatula. The completion of reaction was confirmed by dissolving a small amount of the solid in deionized water and raising the pH of the aqueous solution to 8 using dilute aqueous sodium hydroxide. The solution stayed clear with no precipitate of amidoamine evident, indicating completion of reaction to form primarily a mixture of the amphoteric fluoroaliphatic surfactants:

and

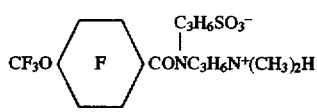

Example 22

Example 22, a mixture of the amphoteric fluoroaliphatic surfactants:

and

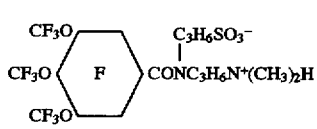

was prepared using the same procedure as described for Example 21 except that 0.0217 mole of the compound made in Example 13 was substituted for 0.0217 mole of the compound made in Example 11.

Comparative Example C9

Comparative Example C9, a mixture of the amphoteric fluoroaliphatic surfactants:

and

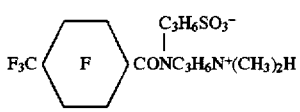

was prepared using the same procedure as described for Example 21 except that 0.0217 mole of the compound made in Comparative Example C4 was substituted for 0.0217 mole of the compound made in Example 11.

Example 23

12.16 g (0.02 mole) of the compound made in Example 13, 9.1 g of isopropanol and 1.77 g (0.022 mole) of 2-chloroethanol were added to a 3-necked round-bottom flask equipped with a stirrer, thermometer and water condenser. This mixture was reacted by stirring and refluxing the contents of the flask for 7.5 hours. The contents were then allowed to cool and were evaporated to dryness using a rotary evaporator to give a yellow oil. Using infrared spectroscopy, the structure of the desired product was confirmed to be the cationic fluoroaliphatic surfactant:

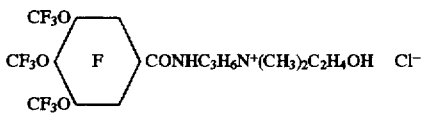

Example 24

Example 24:

was prepared using the same procedure as described for Example 23 except that 0.02 mole of the compound made in Example 14 was substituted for 0.02 mole of the compound made in Example 13.

Example 25

Example 25:

was prepared using the same procedure as described for Example 23 except that 0.02 mole of the compound made in Example 12 was substituted for 0.02 mole of the compound made in Example 13.

Example 26

Example 26:

was prepared using the same procedure as described for Example 23 except that 0.02 mole of the compound made in Example 11 was substituted for 0.02 mole of the compound made in Example 13.

Example 27

6.08 g (0.01 mole) of the compound made in Example 13, 10.0 g of ethanol and 1.92 g (0.01 mole) of citric acid were added to a 3-necked round-bottom flask equipped with a stirrer, thermometer and water condenser. This mixture was heated to boiling with stirring and was allowed to reflux for 5 minutes until a homogeneous solution resulted. This solution was then poured into a glass tray and was evaporated to dryness using a vacuum oven set at 60°–70° C. to give the desired amine salt:

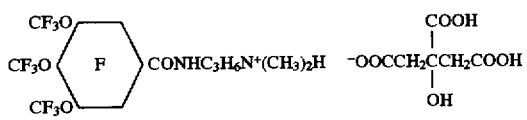

Example 28

Example 28:

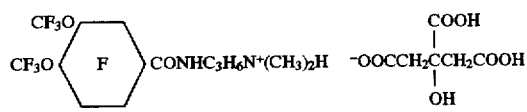

was prepared using the same procedure as described for Example 27 except that 0.01 mole of the compound made in Example 12 was substituted for 0.01 mole of the compound made in Example 13.

Example 29

30.0 g (0.05 mole) of Carbowax™ 600 (a 600 molecular weight polyethylene glycol, available from Union Carbide Corp.) and 50 g of isopropyl ether were added to a 3-necked round-bottom flask equipped with a stirrer. The mixture was stirred while 26.9 g (0.05 mole) of the compound made in Example 3 was added over a 10-minute period, then the mixture was heated to reflux and stirred at this temperature for 2 hours. The ether solvent was evaporated off using a rotary evaporator to produce 40.0 g of a viscous opaque liquid. Infrared spectral analysis was consistent with the following structure:

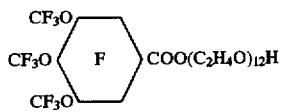

Example 30

82.5 g (0.11 mole) of Carbowax™ 750 (a 750 molecular weight polyethylene glycol monomethyl ether, available from Union Carbide Corp.) and 100 g of isopropyl ether were added to a 3-necked round-bottom flask equipped with a stirrer. The mixture was stirred while 53.8 g (0.1 mole) of the compound made in Example 3 was added over 20 minutes. The resulting mixture was heated to reflux and stirred at this temperature for 2 hours. The ether solvent was evaporated off using a rotary evaporator to produce 104.0 g of a white, waxy solid. Infrared spectral analysis was consistent with the following structure:

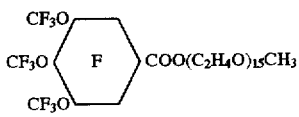

Example 31

2.68 g (0.02 mole) of 2,2-dimethylolpropionic acid and 5.0 g of N,N-dimethylformamide were added to a 3-necked flask equipped with stirrer, thermometer and condenser. The mixture was stirred to form a suspension, and 21.52 g (0.04 mole) of the compound made in Example 3 was added all at once, causing an exotherm to 45° C. The contents of the flask were heated to reflux (approximately 95° C.) for 3 hours, then material was allowed to distill off (believed to be non-functional fluorinated inerts) until the temperature of the contents rose to 135° C. Then 75 g of cold deionized water was added, and the mixture was stirred vigorously for 10 minutes at ambient temperature. The top aqueous phase, containing reaction by-products, was decanted from the bottom yellow liquid product phase, containing the desired product. The bottom phase was then further purified by washing twice with 75 g aliquots of fresh deionized water, each time using vigorous stirring and carefully decanting the top aqueous wash layer. The washed bottom phase was dried by pouring the phase into a glass tray and placing the tray for 3 hours in a water-aspirator vacuum oven set at 65° C. After drying, 16.2 g of viscous, light amber oil was obtained, which according to infrared spectroscopy was consistent with the structure:

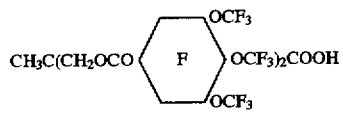

The acid was neutralized with an equivalent amount of aqueous sodium hydroxide and diluted with water to give an aqueous solution of the corresponding sodium carboxylate anionic surfactant to be used for further testing.

Comparative Example C10

3.35 g (0.025 mole) of 2,2-dimethylolpropionic acid and 5.0 g of N,N-dimethylformamide were charged to a 3-necked flask equipped with a stirrer, thermometer and water condenser and were stirred to form a suspension. Then 27.4 g (0.05 mole) of the compound made in Comparative Example C2 was added all at once. The mixture, exotherming to 70° C. to form a homogeneous solution, was stirred at room temperature for 2 hours. Then the temperature was heated to boiling, raising the temperature of the contents of the flask from 70° C. to 135° C. and boiling off nonfunctional inert fluorocarbons which were impurities in the carbonyl fluoride. 75 g of cold deionized water was added and the mixture was stirred vigorously for 10 minutes at ambient temperature. The top water layer was decanted and the saved dense bottom phase was rinsed twice with 75 g aliquots of water. Then 25 g of toluene was added and residual water was azeotroped off by refluxing the toluene solution at 135° C. 17.3 g of thick oil was recovered and, by IR and NMR testing, was found to be:

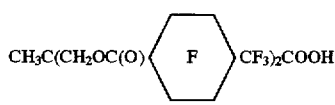

The acid was neutralized with an equivalent amount of aqueous sodium hydroxide and diluted with water to give an aqueous solution of the corresponding sodium carboxylate anionic surfactant to be used for further testing.

The fluoroaliphatic surfactants prepared in the Examples and Comparative Examples above were dissolved in deionized water at various solids concentrations and the surface tension of each surfactant aqueous solution was measured using a K-12 Processor Tensiometer and 665 Dosimat™ measuring method (available from Krüss Corp.). The critical micelle concentration (CMC) (i.e., the concentration at which further surface tension reduction no longer occurred with increasing surfactant added) was determined for each surfactant. The critical micelle concentration for each surfactant and the corresponding surface tension are presented in Table 1.

TABLE 1

| Ex. | Subst. Groups on Fluorinated Cyclohexyl Ring | Surfactant Type | Surface Tension (dynes/cm) | Surfactant Concentration (ppm) |
| --- | --- | --- | --- | --- |
| 15 | 3,4,5-tri CF$_3$O | amine oxide | 16.7 | 100 |
| 16* | 3,4,5-tri CF$_3$O | amine oxide | 16.8 | 200 |
| 17 | 3,4-di CF$_3$O | amine oxide | 16.3 | 500 |
| 18 | 4-mono CF$_3$O | amine oxide | 18.1 | 800 |
| C5 | — | amine oxide | 30.2 | 500 |
| C6 | 4-mono CF$_3$ | amine oxide | 20.0 | 600 |
| 19 | 3,4,5-tri CF$_3$O | acrylic acid adduct | 17.0 | 400 |
| 20* | 3,4,5-tri CF$_3$O | acrylic acid adduct | 16.9 | 400 |
| C7 | 4-mono CF$_3$ | acrylic acid adduct | 22.2 | 1000 |
| C8 | — | acrylic acid adduct | 34.9 | 1000 |
| 21 | 4-mono CF$_3$O | sultone adduct | 19.9 | 1000 |
| 22 | 3,4,5-tri CF$_3$O | sultone adduct | 17.5 | 150 |
| C9 | 4-mono CF$_3$ | sultone adduct | 24.8 | 1000 |
| 23 | 4-mono CF$_3$O | hydroxyethyl quat. | 18.2 | 1000 |
| 24 | 3,4-di CF$_3$O | hydroxyethyl quat. | 22.4 | 250 |
| 25 | 3,4,5-tri CF$_3$O | hydroxyethyl quat. | 17.9 | 500 |
| 26* | 3,4,5-tri CF$_3$O | hydroxyethyl quat. | 19.1 | 1000 |
| 27 | 3,4-di CF$_3$O | citric acid salt | 19.2 | 1000 |
| 28 | 3,4,5-tri CF$_3$O | citric acid salt | 16.6 | 500 |
| 29 | 3,4,5-tri CF$_3$O | POE adduct | 23.6 | 500 |
| 30 | 3,4,5-tri CF$_3$O | methoxy POE adduct | 21.6 | 40 |
| 31 | 3,4,5-tri CF$_3$O | di-R$_f$ carboxylate | 23.2 | 1000 |
| C10 | 4-mono CF$_3$ | di-R$_f$ carboxylate | 25.7 | 1000 |

*Examples 16, 20 and 26 were derived from carbonyl fluorides that were made by direct fluorination with F$_2$. All other examples and comparative examples were derived from carbonyl fluorides that were made by electrochemical fluorination with HF.

The data in Table 1 show that for all the perfluorocycloalkane carbonyl surfactants evaluated, those with trifluoromethoxy groups attached to the perfluorocyclohexane ring showed greater surface activity than those with perfluoromethyl or no perfluorinated groups attached. Also, surfactants with three trifluoromethoxy groups attached to the perfluorocyclohexane ring were more surface active than surfactants with two trifluoromethoxy groups attached to the perfluorocyclohexane ring, which in turn were more surface active than surfactants containing only one trifluoromethoxy group attached to the perfluorocyclohexane ring. This remarkable surface activity is surprising as greatest surface activity is normally achieved with rod-like hydrophobic groups, such as with straight (i.e., non-branched) perfluorinated carbon chains of from 6 to 10 carbons in length. The method of fluorination (electrochemical fluorination with hydrogen fluoride vs. direct fluorination with elemental fluorine) led to little difference in the surface activity of the fluoroaliphatic surfactants.

Aqueous Film-forming Foam Concentrate Formulation and Evaluation

Example 32

An aqueous film-forming foam (AFFF) concentrate was prepared by mixing 4.0% (wt) of the fluoroaliphatic amine oxide surfactant prepared in Example 15, 7.0% (wt) of Sipex™ SOS (sodium octyl sulfate, 33% active, available from Rhone-Poulenc Corp.), 3.0% (wt) Witcolate™ 7093 (a mixture of sodium octyl ether sulfate and sodium decyl ether sulfate, 38% active, available from Witco Corp.), 30.0% (wt) of dipropylene glycol n-propyl ether and 56% (wt) of deionized water. The concentrate pH was adjusted to 8 with aqueous NaOH. The concentrate was evaluated as fresh water (i.e., tap water) and sea water premixes by diluting 3 parts by weight with 97 parts by weight of either fresh water or synthetic sea water (ASTM D1141-52) and evaluating the premixes using several key qualification tests listed in the U.S. Government Military Specification MIL-F-24385 (Revision C) for AFFF concentrates. These tests were: foam expansion (i.e., volume of foam divided by volume of liquid used to make foam), foam 25% drain time (the time it takes for 25% of the liquid in the foam to drain to the bottom of the test graduated cylinder), and vapor seal (a test which determines how well the aqueous film from a premix seals the vapors on the surface of cyclohexane, a flammable fuel). The results from this evaluation along with minimum specification requirements are shown in Table 2.

TABLE 2

| MIL-F-24385 AFFT Test | MIL-F-24385 Section No. | 3% Fresh Water Premix | 3% Sea Water Premix | Minimum Requirement |
| --- | --- | --- | --- | --- |
| 2 gpm foam expansion | 4.7.5 | 6.6 | 6.0 | 5.0 |
| 25% drain time (sec) | 4.7.5 | 212 | 210 | 150 |
| Vapor seal* | N/A | Pass | Pass | Pass |

*The film formation and sealability test used for evaluation describes the generation of an aqueous film by the gentle application of 0.75 mL of premix solution, over 30 to 60 seconds, down the thread of an inverted No. 8 flathead wood screw placed in the center of a 20 cm diameter glass petri dish containing 40 mL of cyclohexane (Baker Analyzed ™ Cyclohexane Reagent, #9206-05, Assay-100%, surface tension = 24.5 dynes/cm, available from J.T. Baker Chem. Co., Phillipsburg, N.J.). Two minutes after applying the first drop of premix solution, a small flame is held over the perimeter of the cyclohexane surface; for a passing vapor seal, no sustained ignition results.

The data in Table 2 show that this AFFF concentrate, containing the surfactant prepared in Example 15 as the only fluoroaliphatic surfactant, when diluted to 3% premixes gave good foam expansion, drain time and vapor sealing performance in the standard AFFF government tests and would be expected to perform well as an extinguishing agent for hydrocarbon flammable liquid fires.

We claim:

1. A composition comprising a perfluoro (alkoxycycloalkane) carbonyl group-containing surfactant according to the formula:

[(A_fY)_x(Q)(Z)_x]

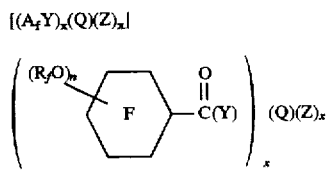 (Q)(Z)_x wherein:

$R_f$ is independently selected from 1 to 4 carbon atoms; and n is an integer from 1 to 5 inclusive with the proviso that when one or more $R_f$ contains from 3 to 4 carbon atoms, n is 1 to 3;

Y is an oxygen or a sulfur atom or is an N(R') group where R' is selected from the group of substituents consisting of: a hydrogen atom, a lower alkyl group, and groups comprising a water-solubilizing polar group that contains an anionic, cationic, nonionic, or amphoteric moiety connected to the nitrogen atom by a multivalent linking group Q;

Q is a multivalent linking group selected from the group consisting of alkylene, arylene, a combination of alkylene and arylene, oxydialkylene, thiodialkylene, and a single bond;

Z is a water-solubilizing polar group containing an anionic, cationic, nonionic, or amphoteric moiety or any combination thereof; and x is independently 1 or 2;

wherein Y and Z are each bonded to O or Y is bonded to Z when Q is a single bond.

2. The composition of claim 1 wherein the perfluoro (alkoxycycloalkane) carbonyl group-containing surfactant is an amine oxide.

3. The composition of claim 1 wherein the perfluoro (alkoxycycloalkane) carbonyl group-containing surfactant is an amine oxide of the formula:

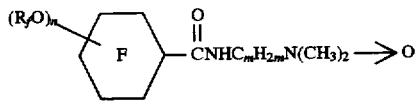

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

4. The composition of claim 1 wherein the perfluoro (alkoxycycloalkane) carbonyl group-containing surfactant is an amine oxide of the formula:

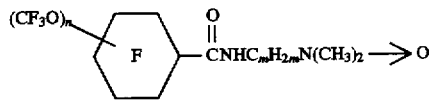

wherein n is an integer from 1 to 5 inclusive and m is inclusively an integer between 2 and 4.

5. The composition of claim 1 wherein the perfluoro (alkoxycycloalkane) carbonyl group-containing surfactant is an amine oxide of the formula:

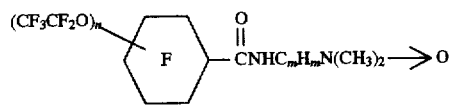

wherein n is an integer from 1 to 5 inclusive and m is inclusively an integer between 2 and 4.

6. The composition of claim 1 wherein the perfluoro (alkoxycycloalkane) carbonyl group-containing surfactant is of the formula:

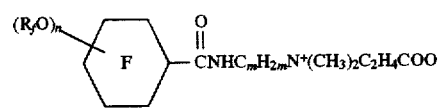

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

7. The composition of claim 1 wherein the perfluoro (alkoxycycloalkane) carbonyl group-containing surfactant is of the formula:

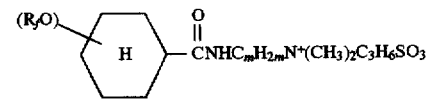

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

8. The composition of claim 1 wherein the perfluoro (alkoxycycloalkane) carbonyl group-containing surfactant is of the formula:

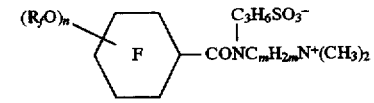

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

9. The composition of claim 1 wherein the perfluoro (alkoxycycloalkane) carbonyl group-containing surfactant is of the formula:

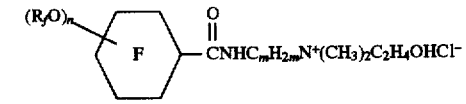

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

10. The composition of claim 1 wherein the perfluoro (alkoxycycloalkane) carbonyl group-containing surfactant is of the formula:

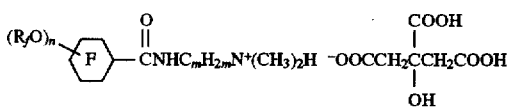

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

11. The composition of claim 1 wherein the perfluoro(alkoxycycloalkane) carbonyl group-containing surfactant is of the formula:

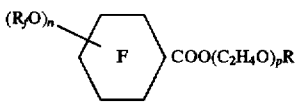

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; p is inclusively an integer between 5 to 20; and R is a hydrogen atom or is a lower alkyl group.

12. The composition according to claim 1 wherein the multivalent linking group Q is ethylene, propylene or isobutylene.

13. An aqueous film-forming foamable composition comprising one or more perfluoro(alkoxycycloalkane) carbonyl group-containing surfactants according to claim 1 and one or more water-soluble fluorine-free surfactants selected from the group consisting of nonionic hydrocarbon containing surfactants with a hydrophilic-lipophilic balance (HLB) value greater than or equal to about 10 and ionic hydrocarbon-containing surfactants having a carbon chain length containing inclusively from about 6 to about 16 carbon atoms.

14. The composition of claim 13 wherein one or more of the perfluoro(alkoxycycloalkane) carbonyl group-containing surfactants is an amine oxide.

15. The composition of claim 13 wherein one or more of the perfluoro(alkoxycycloalkane) carbonyl group-containing surfactants is according to the formula:

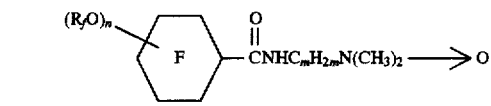

wherein $R_f$ is independently selected as a perfluoroalkyl group having from 1 to 4 carbon atoms; n is an integer from 1 to 5 inclusive with the proviso that when $R_f$ contains from 3 to 4 carbon atoms, n is less than or equal to 3; and m is inclusively an integer between 2 and 4.

16. The composition of claim 13 wherein the non-ionic hydrocarbon-containing surfactants are selected from the group consisting of: ethylene oxide-based nonionic surfactants, ethoxylated alkylphenols, and block copolymers of ethylene oxide and propylene oxide; and wherein the short-chain ionic hydrocarbon-containing surfactants are selected from the group consisting of: alkyl sulfates, alkyl ether sulfates, alkyl sulfonates, salts of an n-octyl sulfate and sodium decyl sulfate, and imidazole-based surfactants.

17. The composition of claim 13 further comprising a water soluble solvent.

18. The composition of claim 17 wherein the water soluble solvent is selected from the group consisting of ethylene glycol, glycerol, dipropylene glycol mono-n-propyl ether, dipropylene glycol monomethyl ether, propylene monobutyl ether, and hexylene glycol.

19. The composition of claim 13 further comprising a stabilizer or thickener.

20. The composition of claim 19 wherein the stabilizer or thickener is selected from the group consisting of partially hydrolyzed proteins, starches, polyvinyl resins, polyvinyl pyrolidone, polyacrylamides, carboxyvinyl polymers, alkanol amides, long chain alkanols, polysaccharide resins, and poly(oxyethylene) glycol.

* * * * *

UNITED STATES PATENT AND TRADEMARK OFFICE
CERTIFICATE OF CORRECTION

PATENT NO. : 5,756,000
DATED : May 26, 1998
INVENTOR(S) : John C. Hansen et al.

It is certified that error appears in the above-identified patent and that said Letters Patent is hereby corrected as shown below:

Col. 10, lines 50-54, kindly delete the formula printed and replace with

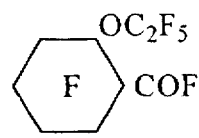

Signed and Sealed this

Twenty-second Day of June, 1999

Attest:

Q. TODD DICKINSON

Attesting Officer    Acting Commissioner of Patents and Trademarks